United States Patent [19]
DeWeerd et al.

[11] Patent Number: 5,484,729
[45] Date of Patent: Jan. 16, 1996

[54] MICROBIAL DECHLORINATION OF POLYCHLORINATED BIPHENYL COMPOUNDS

[75] Inventors: Kim A. DeWeerd, Rexford; Donna L. Bedard, Loudonville, both of N.Y.

[73] Assignee: General Electric Company, Schenectady, N.Y.

[21] Appl. No.: 376,485

[22] Filed: Jan. 20, 1995

Related U.S. Application Data

[63] Continuation of Ser. No. 73,400, Jun. 7, 1993, abandoned.

[51] Int. Cl.$^6$ .............................. B09B 3/00; C12N 1/38; C02F 3/00
[52] U.S. Cl. ...................... 435/262.5; 435/244; 210/610; 405/264
[58] Field of Search .................. 435/262.5, 262, 435/244; 210/601, 610, 612, 909; 405/264

[56] References Cited

U.S. PATENT DOCUMENTS

| | | | |
|---|---|---|---|
| 4,584,102 | 4/1986 | Bogart et al. | 210/610 |
| 4,663,027 | 5/1987 | Mendiratta et al. | 208/262 |
| 4,664,805 | 5/1987 | Focht | 210/611 |
| 4,843,007 | 6/1989 | Bedard et al. | 435/252.1 |
| 4,876,201 | 10/1989 | Bedard et al. | 435/262 |
| 5,227,069 | 7/1993 | Van Dort et al. | 210/610 |

OTHER PUBLICATIONS

Brown et al., "Environmental Dechlorination of PCBs", *Environmental Toxicology and Chemistry*, vol. 6, pp. 579–593 (1987).
Horowitz et al., Reductive "Dehalogenations of Halobenzoates by Anaerobic Lake Sediment Microorganisms", *Applied and Environmental Microbiology*, vol. 45, No. 5 (May 1993), pp. 1459–1465.
Sundström et al., "The Metabolism of Chlorobiphenyls", in *Chemosphere*, vol. 5, Pengamon Press Ltd., New York, (1976), pp. 267–298.
Parsons et al., "Biodegradation of chlorinated biphenyls and benzoic acids by a Pseudomonas strain", CA Abstract AN 109:167064 from Applied Microbiol. Biotechnol., 29(1), pp. 81–84 (1988).

*Primary Examiner*—William H. Beisner
*Assistant Examiner*—T. J. Reardon
*Attorney, Agent, or Firm*—James Magee, Jr.

[57] ABSTRACT

An improved process for anerobic microbial dechlorination of polychlorinated biphenyl compounds in sediment containing microorganisms capable of dechlorinating polychlorinated biphenyls which includes adding and admixing the sediment with a halogen substituted benzoic acid, salicylic acid or a lower alkyl ester of the acids.

5 Claims, 6 Drawing Sheets ations is usually
MICROBIAL DECHLORINATION OF POLYCHLORINATED BIPHENYL COMPOUNDS This application is a continuation of application Ser. No. 08/073,400, filed Jun. 7, 1993, now abandoned.

FIELD OF THE INVENTION

The present invention relates generally to methods for dechlorination of polychlorinated biphenyl compounds (PCBs) and particularly to microbial dechlorination of highly chlorinated PCB compounds. Particular embodiments of the invention are directed to decontamination of materials such as marine sediments, sand and soil which are contaminated with PCBs and to bioremediation of environmental sites such as landfills, waste sites, lakes, ponds, and stream beds or sediments containing PCBs.

BACKGROUND OF THE INVENTION

PCBs had often been used in the past as dielectric fluids in electrical equipment because they possessed a variety of very useful properties. However, their environmental persistence eventually resulted in a ban on such use. Because of the toxicity of the compounds, it has become necessary to devise techniques to eliminate or minimize the amounts of PCBs in the environment.

An illustrative chemical technique for reducing the level of PCBs present in organic solvents such as transformer oil is described in U.S. Pat. No. 4,663,027 for A. Mendiratta et al, and involves the addition of a combination of glycol and alkali metal hydroxide to form a reactive mixture. However, this type of direct chemical treatment is often not practical when the PCBs are located in areas such as landfill sites, river beds, and sewage sludge.

Another procedure for treating halogenated aromatics in organic waste is described in U.S. Pat. No. 4,477,570 issued to Colaruotolo et al. This patent teaches that microorganisms have been identified which have the capability of efficiently utilizing various aromatic organic chemicals as carbon sources for growth. Furthermore, it has been shown that some microorganisms are capable of growing in the presence of chlorinated aromatic compounds. However, PCBs which exist in weathered environmental soil often contain five or more chemically combined chlorine atoms per molecule, indicating that these types of compounds generally resist biodegradation.

In addition to the number of chlorine atoms per biphenyl nucleus, the location of chlorine atom substitution on the biphenyl nucleus is also an important factor influencing the resistance of PCBs to biodegradation. The positions at which chlorine may be attached to a biphenyl nucleus are shown below:

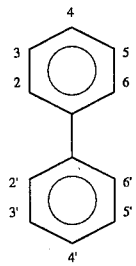

Reductive dechlorination of PCBs proceeds by stepwise removal of chlorines from the biphenyl nucleus. They are replaced by hydrogen atoms. When achieved by biological means, reductive dechlorination has practical value for effective clean-up with minimal ecological damage.

Dechlorination of PCBs in the environment by removal of meta and para chlorines has been reported for freshwater, estuarine, and marine sediments. This dechlorination has been attributed to anaerobic bacteria which exist in the sediments. However, the rate of dechlorination is usually slow, taking years or even decades.

The microbial population that resides in anaerobic sediments is very diverse. The microorganisms that are capable of dechlorinating PCBs may be only a small fraction of the total population. Since all of the microorganisms compete for the limited nutrients that are available, only those which have a biological advantage will actively grow. Such an advantage can result from the ability to use available nutrients more efficiently than competing organisms. An advantage can also result from an ability to utilize, for food or energy, compounds that other microorganisms cannot utilize in the same manner.

Certain PCBs, such as Aroclor 1260, which is a mixture of polychlorinated biphenyls comprised mainly of hexa- and heptachlorobiphenyls, are difficult substrates for microbial attack. In many environmental sites, only slight dechlorination of the PC Bs has occurred naturally. However, as reported by Bedard et al, in the Ninth Progress Report (1990) of General Electric Company's Research and Development Program for the destruction of PCBs, individual PCB congeners, such as 2,3,4,5,6-pentachlorobiphenyl, have been found to be capable of stimulating dechlorination of Aroclor 1260 in sediment by indigenous anaerobic microorganisms. Unfortunately, the addition of PCB congeners to a contaminated site is not an acceptable means of bioremediation because PCBs are regulated. Furthermore, in most instances, the PCB congener is not totally dehalogenated to biphenyl. Moreover the anaerobic microorganisms do not degrade the biphenyl nucleus which remains in the environment.

There is therefore a need in the art for an acceptable method of stimulating and accelerating microbial dechlorination of PCBs in aqueous sediments under anaerobic or low-oxygen conditions.

SUMMARY OF THE INVENTION

The present invention addresses the needs mentioned above by providing an improved method for accelerating microbial dechlorination of PCBs under anaerobic conditions in the sediment of bodies of water and in aqueous slurries of sand or soil which contains microorganisms capable of dechlorinating PCBs. The method of this invention comprises admixing with the sediment at least one bromine or iodine substituted compound selected from the group consisting of benzoic acid, salicylic acid, and esters thereof.

In addition to accelerating dechlorination, the process of this invention is advantageous because the benzoic and salicylic add compounds are readily available, and are easily biodegradable.

By the practice of this invention dehalogenation of polychlorinated biphenyls, particularly hexachloro- and heptachlorobiphenyls, can be achieved when brominated or iodinated compounds are added to the PCB-contaminated sediment or to an aqueous soil slurry. Accordingly, sediments contaminated with PCBs having an average of about 3 to 9 chlorine atoms per biphenyl nucleus can be reduced by an average of up to one or more chlorines per biphenyl nucleus which includes the elimination or reduction of a significant amount of the more highly chlorinated biphenyls. Substantial reduction or elimination of the more highly chlorinated PCBs is deemed to have been effected when a decrease of at least 20% of the more highly chlorinated PCBs congeners is shown in a random test sample taken from the material being treated. A decrease in the more highly chlorinated compounds is accompanied by a corresponding increase in the less chlorinated congeners.

The microbial dechlorination of PCBs that is stimulated by the process of the invention does not reduce the total number of PCB molecules, but it does decrease the toxicity, carcinogenicity, and bioaccumulation of the PCBs and increases their susceptibility to further biodegradation by aerobic bacteria and metabolism by higher organisms. Therefore, the microbial dechlorination of PCBs which is stimulated in sediments by the addition to the sediment of halogenated benzoic or salicylic acids or derivatives significantly reduces the health hazard associated with the PCB-containing sediment. The microbial dechlorination process of this invention provides improved dechlorination of highly chlorinated PCB compounds

DETAILED DESCRIPTION OF THE INVENTION

Figure 1:
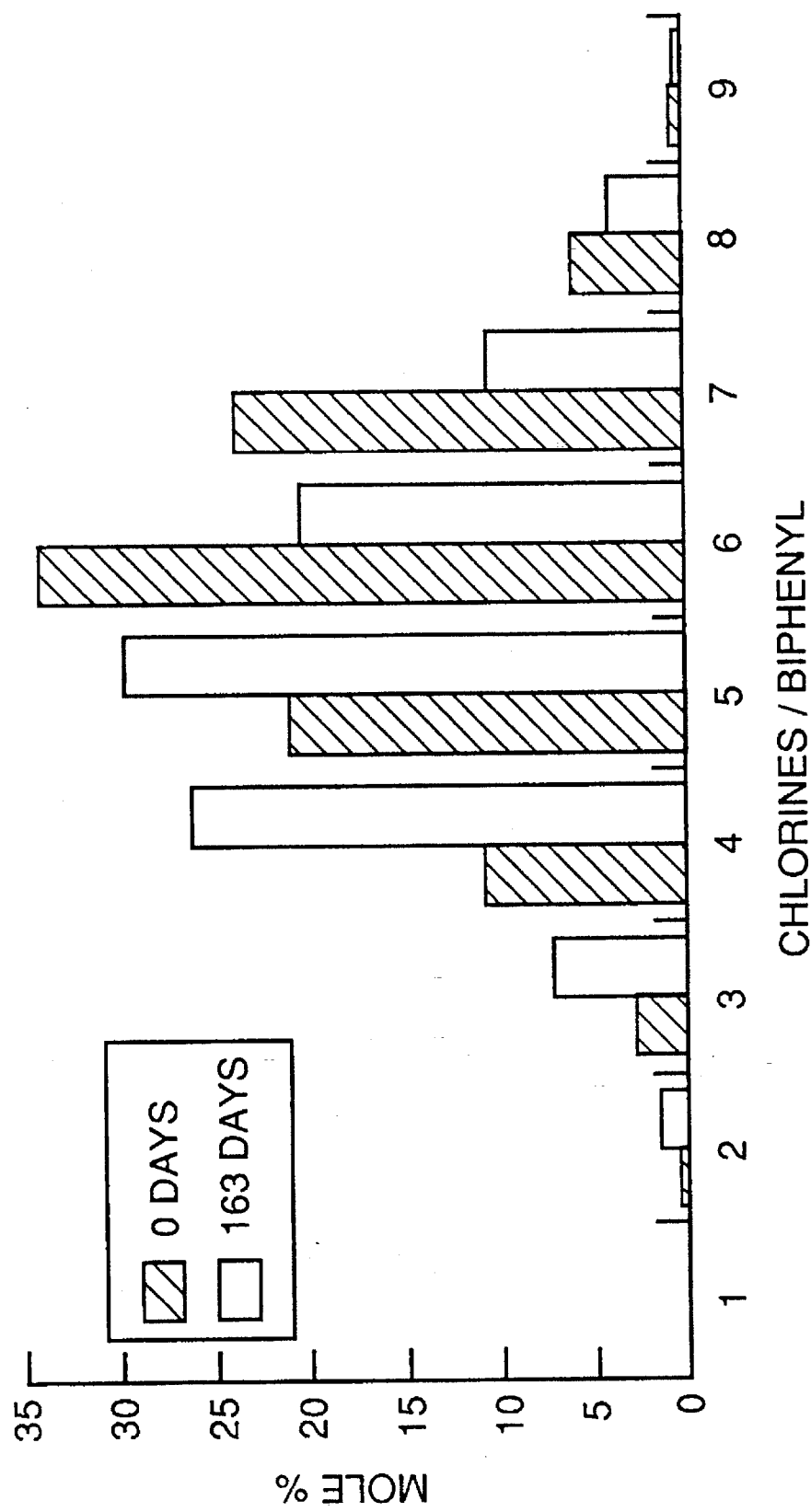
FIG. 1 shows the distribution of PCBs grouped by the number of chlorine atoms per biphenyl nucleus before and after microbial dechlorination and treatment by the method of this invention.

Sediment which is amenable to treatment by the method of the present invention can be found in freshwater, estuarine, and marine environments. The particular sediment must contain microorganisms which dechlorinate PCBs to some extent. This type of sedimentary environment is familiar to those involved with bioremediation, since the gradual, natural dechlorination of PCBs in various ponds, riverbeds and the like has been documented. Accordingly the term "sediment" or any similar word as used herein is intended to include any admixture comprising water and soil or soil-like material such as sand, gravel, or clay, whether naturally occurring or man-made. Sediments can be from the bed or banks of natural or man-made bodies of water including rivers, lakes, ponds oceans, seas, canals and the like. The term is not limited to compacted or dense sediments but includes slurries and any other admixture of water and soil.

Examples of PCBs commonly found in the environment which can be treated by the present invention include commercial mixtures of PCBs such as Aroclor 1016, 1242, 1248, 1254, 1260, 1262 and 1268. These Aroclors can be characterized as follows:

| Arolor | Average Number of Chemically Combined Chlorine Atoms |
|---|---|
| 1016 | 3 |
| 1242 | 3–4 |
| 1248 | 4–5 |
| 1254 | 5–6 |
| 1260 | 6–7 |
| 1262 | 7 |
| 1268 | 8–9 |

A convenient and well recognized method for determining the composition of PCBs in a random sample selected from a sedimentary site is by means of gas chromatograph equipped with a high resolution capillary column and an electron capture detector to obtain a quantitative congener-specific analysis of the PCBs calibrated against a mixture of Aroclors having a known composition.

The halogen-substituted compounds which are utilized in the present invention are benzoic acid and ortho hydroxy benzoic acid also known as salicylic acid and derivatives of these compounds, such as their alkyl esters. The halogen substituents are preferably selected from the group consisting of chlorine, bromine, iodine, and combinations thereof. Bromine and iodine are particularly preferred for use in this invention. The choice of sediment and the nature of the particular microorganisms contained therein may influence the choice of particular benzoic or salicylic compounds. As described below, the choice of a particular benzoic or salicylic compound for a particular sediment to be treated can be determined, without undue experimentation by a simple screening technique.

Illustrative examples of the mono- and polyhalogenated compounds suitable for use in this invention are: mono-brominated benzoic compounds such as 2-bromobenzoic acid, 3-bromobenzoic acid; 4-bromobenzoic add; and mixtures thereof. Examples of suitable dibrominated benzoic compounds are 2,5-dibromobenzoic acid; 3,5-dibromobenzoic acid, and mixtures of these compounds and the like.

Examples of suitable mono-iodinated compounds are 2-iodobenzoic acid, 3-iodobenzoic acid, 4-iodobenzoic acid, and mixtures of any of the foregoing. Examples of polyiodo compounds include 2,5-iodobenzoic acid; 2,3,5-iodobenzoic acid; and 3,4,5iodobenzoic acid, and the like.

Halogenated salicylic compounds suitable for some embodiments of this invention include 3,5-dibromosalicylic acid and 5-iodosalicylic acid and the like.

Accordingly halogenated benzoic and salicylic compounds containing from one to five chlorine, bromine, or iodine atoms and combinations of halogens are within the contemplation of the invention.

As mentioned above, esters of the halogenated benzoic or salicylic compounds may also be used in the present invention. For example, it is expected that alkyl benzoates and alkyl salicylates would be effective in some sediments. The alkyl groups forming the ester may be straight-chain or branched, and usually contain about 1 to 12 carbon atoms, and more preferably, about 1 to 5 carbon atoms. Preferred esters include methyl benzoate and methyl salicylate.

For the sake of brevity, the term "benzoic or salicylic compound" will sometimes be used herein; it is meant to cover all of the possible halogenated compounds mentioned above.

The optimum effective amount of the benzoic acid- or salicylic acid-based compound can be determined empirically by a screening procedure as described below. Generally, about 100 micromolar to about 5 millimolar based on the total volume of the water and sediment is preferred to substantially increase the rate and extent of dechlorination.

For some sedimentary sites, nutrients may be advantageously used in combination with the benzoic or salicylic compounds. Suitable nutrients are usually ammonium or alkali metal salts of organic acids adjusted to a pH of about 6 to about 7. Examples include sodium salts of malic, pyruvic, fumaric, succinic, benzoic, formic, and lactic acids; glucose; amino acids; and salts of fatty acids, including acetate, proprionate, butyrate, and hexanoate. An effective concentration of the nutrient is usually in the range of about 0.1 to about 20 mMoles/liter of sedimentary slurry, as described below. Nutrients which may prove beneficial include vitamins, purine and pyrimidine bases, fertilizers, humic acid, hemin, 1,4-naphthoquinone, and the like.

In carrying out the process of this invention, a portion of a sedimentary site can be selected as the bioremediation zone to be treated, and is then enclosed sufficiently to permit the controlled introduction of the benzoic- or salicylic-based compound and optionally, the nutrient. An example of a sufficient enclosure is a structure such as a vertical caisson.

The particular technique for addition of the benzoic or salicylic compound to the sediment is not critical, as long as a substantially uniform dispersion of the compound within the sediment or solid phase of a slurry is achieved. To facilitate handling of the compounds which accelerate dechlorination, the selected benzoic or salicylic acid compound can be admixed with a compatible liquid or solid carrier or vehicle such as water, acetone, methanol, diatomaceous earth, and the like. Carriers which are suitable should (1) be miscible with water; (2) solubilize the benzoic or salicylic compound; (3) be biodegradable; and (4) be nontoxic to most of the microorganisms in the sediment which are responsible for dechlorination.

Agitation may be used to insure uniform dispersion of the benzoic or salicylic compound in the aqueous slurry of sediment.

The temperature of the aqueous slurry during the incubation period, i.e., after dispersion of the benzoic or salicylic compound, should be maintained in the range of about 5° to about 55° C. In more preferred embodiments, the temperature should be in the range of about 5° to about 40° C. In some especially preferred embodiments, maximum effectiveness in terms of dechlorination is achieved at a temperature in the range of about 15° C. to about 30° C. Selection of the most appropriate temperature will depend on various factors, such as the nature of the particular sediment; its location; the climate; the extent of PCBs present; the types of PCBs e.g., moderately or highly chlorinated present and their individual concentrations; and the indigenous microbial populations present.

The optimum effective period of time for continuation of the treatment by this invention will vary considerably, and also depends on the factors described above. In general, treatment is deemed satisfactory if and when there is at least about a 20% decrease in the level of more highly chlorinated PCBs in the sedimentary sample being treated, i.e., a decrease in the total amount of the most highly chlorinated PCBs in the PCB mixture being treated.

Most often, the minimum time period for satisfactory treatment is about 50 days. The period often is extended to about 360 days. Those skilled in the art can determine the most appropriate period for satisfactory treatment of a particular sedimentary sample by using the technique described above for periodic analysis of PCB levels in portions of the sample. In the field it is expected that times of from 3 to 4 months to 2 to 3 years could be required to achieve the required degree of remediation.

As mentioned above, the sediment being treated according to this invention must contain some microorganisms which are capable of naturally dechlorinating PCBs. If such microorganisms are not naturally present, the sediment or slurry can be inoculated with an inoculum from a sediment or soil known to contain PCB dechlorinating microorganisms. Those in the art are well aware of the techniques for preparing cultures and preparing inoculum for treating various substrates. The reaction which removes halogen from the PCB also appears to result in dehalogenation of the added benzoic or salicylic compounds.

Determination of whether a particular sediment contains the necessary microorganisms and is therefore amenable to treatment by this invention can be made by a straightforward screening procedure, as described below. In brief, a random sample is first taken from a sedimentary site known to contain PCBs. The benzoic or salicylic compound is added to the sample in an effective amount, as described above. The resulting mixture is maintained within a temperature range as described above for the overall process. Agitation of the sediment is also sometimes useful.

The initial selection of a random sample from the contaminated site is to determine the feasibility of applying the method of the present invention to bioremediate the identified contaminated area. Although the initial screening procedure can generally be conducted at ambient temperatures, in some instances depending upon stitch factors as the nature of the sediment, its location, the extent of PCB contamination, the particular PCBs present and their concentration, and the indigenous microbial populations present, temperatures in the range of 20° C. to 30° C. can be used. Agitation of the sediment during treatment, such as by stirring, can also be necessary in particular instances.

The mixture is allowed to incubate anaerobically for a period of at least 50 to 100 days. At that point, a sample is taken and analyzed to determine if there is a decrease of at least about 20% in the level of more highly chlorinated PCBs. If the decrease has been achieved, the site can then be subjected to full-scale treatment according to the procedure outlined above. This invention is also useful for remediation of non-sediment or dry soils and sands contaminated with PCBs. Dry material from a landfill site can be excavated slurried and treated in treatment tanks, natural ponds or lagoons or man-made ponds which have been inoculated with the microorganisms and the benzoic acid or salicylic acid compounds disclosed herein. Suitable inoculum can be prepared by known procedures from sediments taken from sites known to contain PCB dechlorinating mircoorganisms.

The following examples are provided to more fully describe this invention. They should be considered as illustrative of the invention, rather than limiting what is otherwise disclosed and claimed herein. All parts and percentages are based on weight, unless otherwise indicated.

In the following examples, samples of an aqueous sediment containing PCBs were slurried with double-distilled water in a volume ratio for sediment to water of 2:3 inside an anaerobic chamber to minimize oxygen concentration in the slurries. Disodium malate (a nutrient) was then added to each of the slurries in an amount which resulted in a final concentration of 10 mM. One of the following compounds was also added to each of the samples in an amount which resulted in a final concentration of 350 micromolar of 2-bromobenzoic acid; 3-bromobenzoic acid; 4-bromobenzoic acid; 2-iodobenzoic acid; 3-iodobenzoic acid; 4-iodobenzoic acid; 2,5-dibromobenzoic acid; or 3,5-dibromobenzoic acid. The experiments were set up in duplicate with controls sterilized by autoclaving.

Aliquots of the slurries for PCB analysis were sampled every 21 days and extracted with vigorous shaking (24 hours) with anhydrous ether (6 volumes) and elemental mercury (¼ volume, to remove any sulfur which may be present).

The samples containing PCBs were analyzed by gas chromatography (GC) with an electron capture detector and a DB-1 capillary column. The column is available from J & W Scientific, and had dimensions of 30 m long by 0.25 mm,(inside diameter). This type of equipment is also described in "Environmental Dechlorination of PCBs"; J.F. Brown et al; Environ. Toxicol. Chem. 6:579–593; May, 1987.

Aliquots for halobenzoic acid analysis were sampled every week and centrifuged to separate sediment and aqueous phases. The halobenzoic acids and benzoic acid in the aqueous portion were analyzed by high pressure liquid chromatography (HPLC) and spectrophotometric detection. These techniques are described by A. Horowitz et al in Appl. Environ. Microbiol, 45:1459–1465, 1983.

EXAMPLE 1

Autoclaved controls showed no change in PCB levels throughout the experiment. After 20 days, 4-iodobenzoic acid was dehalogenated, resulting in the accumulation of benzoic acid. A second addition of 4-iodobenzoic acid was immediately dehalogenated, resulting in more benzoic acid. The benzoic acid was degraded after approximately 50 days. The dechlorination of PCBs in these samples was first detected after 30 days of incubation.

FIG. 1 shows initial PCB homolog distribution and distribution after 163 days for a sample which was treated with 4-iodobenzoic acid. The amount of chlorinated biphenyl compounds having 6–8 chlorines per biphenyl, typically the PCBs most difficult to degrade, was reduced, while the amount of PCB homologs having 2–5 chlorines per biphenyl increased. Overall, an average of about 1 to 1.5 chlorines per molecule of PCB was removed.

Figure 2:
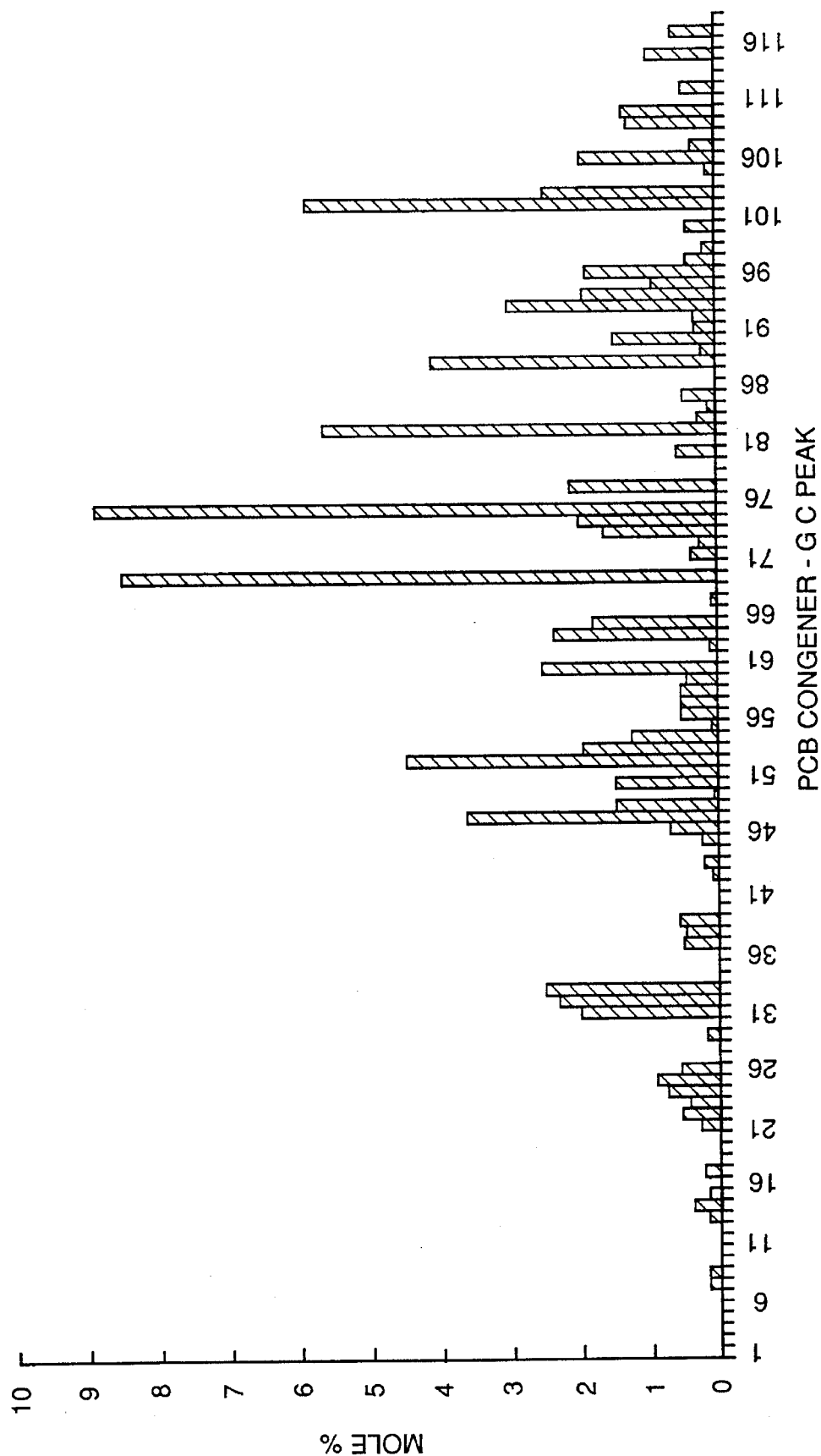
FIG. 2 shows the relative proportions of specific PCB congeners in a sediment sample prior to treatment by the invention.
Figure 2A:
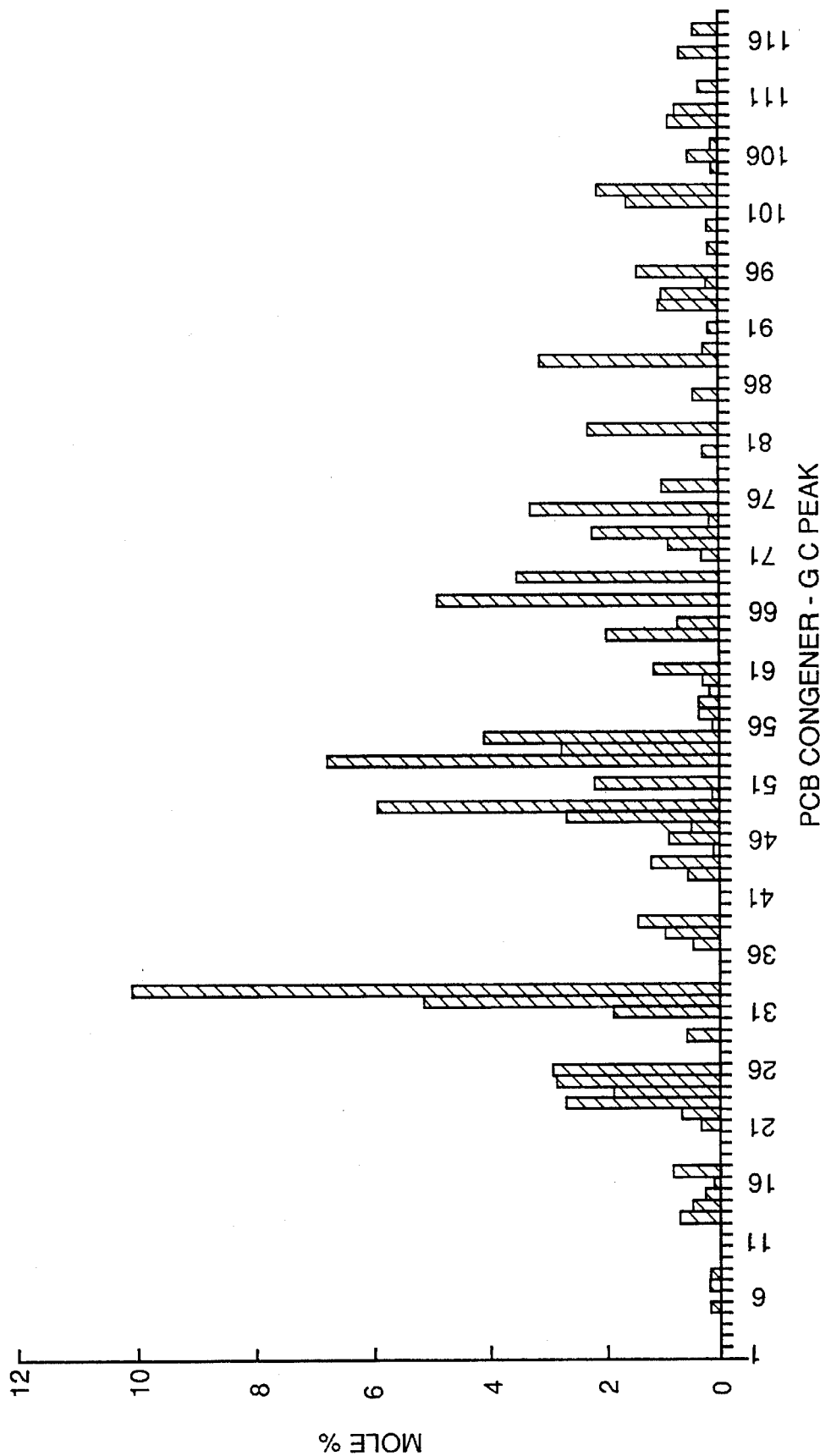
FIG. 2a shows the relative proportions of PCB congeners in a sample of the same sediment after incubation for 163 days after addition of 4-iodobenzoic acid according to the present invention.
Figure 3:
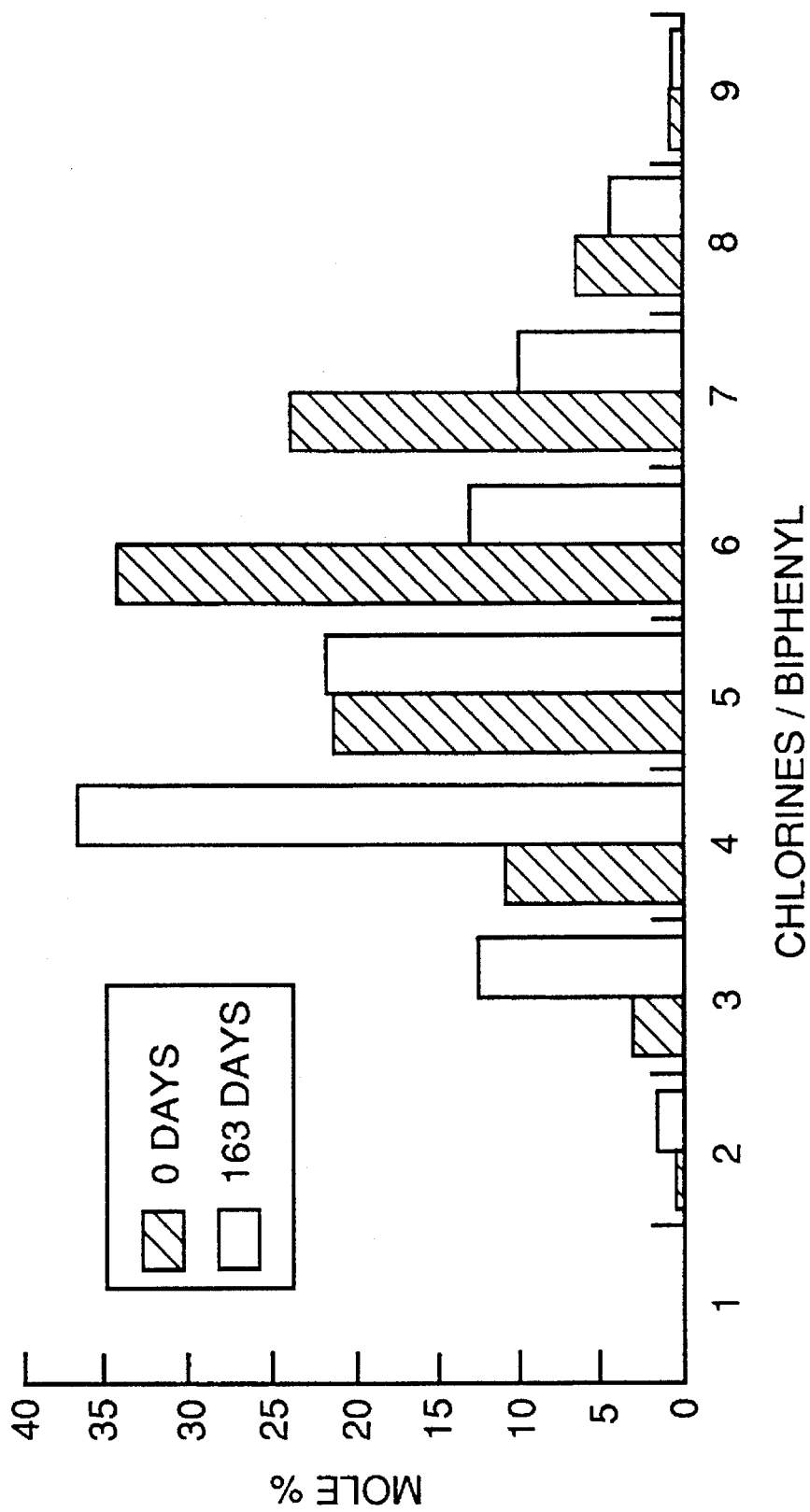
FIG. 3 shows the distribution of PCB homologs before and after microbial dechlorination after treatment with 4-bromobenzoic acid.

FIG. 2, which includes two separate graphs shows the levels of various individual PCB compounds or congeners in a sample as analyzed prior to treatment with 4-iodobenzoic acid, and after 163 days of treatment. The figure demonstrates a considerable decrease in the levels of the following PCB congeners: Peaks 69 (2,3,6,2',4',5'-CB); 75 (2,4,5,2',4', 5'); 82 (2,3,4,2',4',5'-CB); 88 (2,3,4,5,2',4',640 -CB); and 102 (2,3,4,5,2',4',540 -CB). Increases are shown in the levels of the following congeners: Peaks 25 (2,5,2',640 ,-CB); 26 (2,4,2',6'-CB); 32 (2,4,2',5'-CB); 33 (2,4,2',4'-CB); 49 (2,4, 6,2',3'-CB); and 67 (2,3,5,6,2',4'-CB). These types of changes indicate a type of meta, para dechlorination known as "pattern N".

EXAMPLE 2

In the experiment which utilized 4-bromobenzoic acid, this compound was dehalogenated after approximately 40 days, resulting in the accumulation of benzoic acid and bromide. The benzoic acid appeared to be transitory, as evidenced by its lower concentration after 85 days. The bromide released during the dehalogenation reaction accumulated to the original concentration of 4-bromobenzoic acid. The reductive dechlorination of PCBs in these samples was first detected after 60 days incubation.

Figure 4:
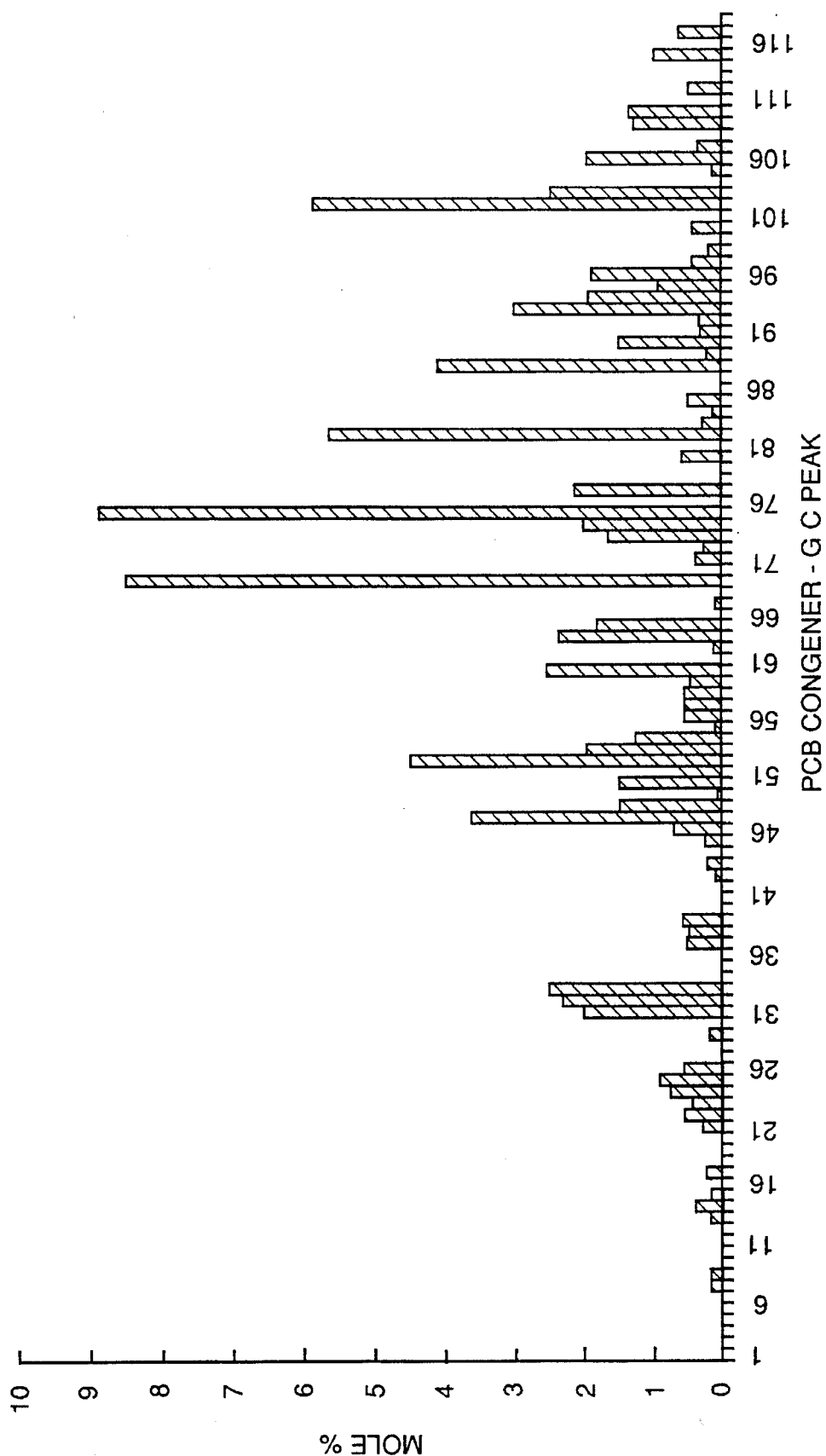
FIG. 4 shows the relative proportions of specific PCB cogeners in a sediment sample prior to treatment by the invention.
Figure 4A:
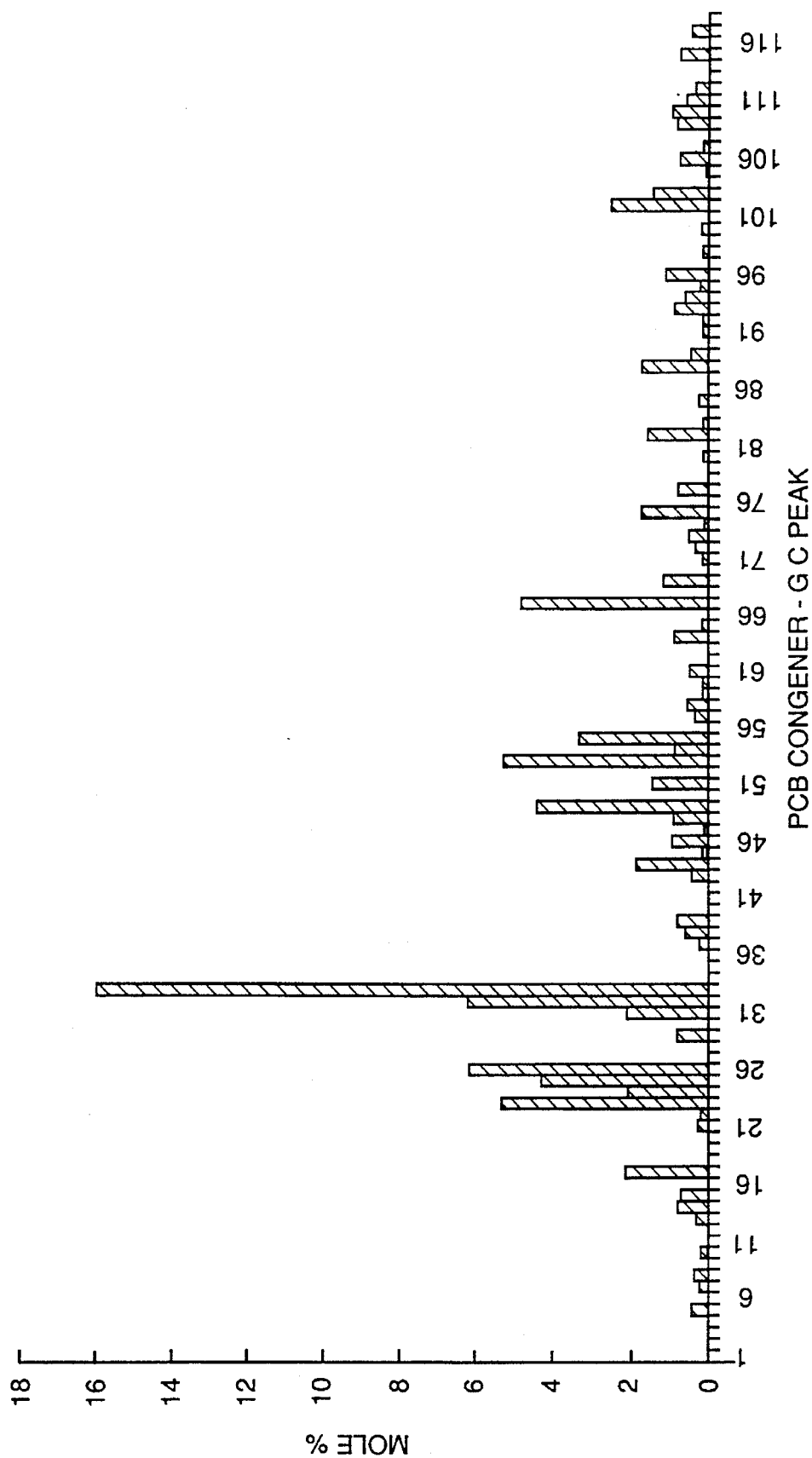
FIG. 4a shows the relative proportions of PCB cogeners in a sample of the same sediment after incubation for 163 days after addition of 4-bromobenzoic acid according to the present invention.

FIGS. 4 and 4A demonstrate that the addition of 4bromobenzoic acid stimulated the same PCB dechlorination pattern as the 4-iodobenzoic acid addition.

While the dehalogenation of 4-bromobenzoic acid was slower than that of 4-iodobenzoic acid, the use of 4-bromobenzoic acid resulted in more extensive dechlorination of the PCBs after 163 days, as compared to the use of 4-iodobenzoic acid.

Other modifications and variations of this invention are possible in view of the description thus provided. It should be understood, therefore, that changes may be made in the particular embodiments shown which are within the scope of the invention defined in the appended claims. All patents and other publications mentioned above are incorporated herein by reference.

What is claimed is:

1. A method for accelerating anaerobic microbial dechlorinmation of more highly chlorinated PCBs in aqueous sediment which contains anaerobic microorganisms capable of dechlorinating PCBs, which comprises the steps of:

(1) proscreening for the presence of anaerobic microorganisms capable of dechlorinating PCBs by
   (a) adding to a portion of the sediment containing PCBs a halogen-substituted acid or acid derivative selected from the group consisting of halogen-substituted benzoic acid, halogen-substituted salicylic acid, and lower alkyl esters thereof having 1 to 5 carbons in the alkyl moiety;
   (b) allowing the resulting admixture to incubate under anaerobic conditions at a temperature between about 5° C. and about 55° C. for a period of about 20 days; and
   (c) measuring the remaining amount of highly chlorinated PCBs; and substantial decrease in the concentration of more highly chlorinated PCBs (2) adding to and admixing with the balance of the sediment an effective amount of at least one halogen-substituted compound selected from the group consisting of halogen-substituted benzoic acid, halogen-substituted salicylic acid, and halogen-substituted esters of said acids having 1 to 5 carbons in the ester group, and incubating the sediment under conditions sufficient to effect dechlorination of said more highly chlorinated PCBs.

2. The method according to claim 1 wherein before dechlorination the aqueous sediment has PCBs having 3 to 9 atoms per molecule and the halogen-substituted compound is added to the aqueous sediment in concentrations ranging from about 100 micromolar to about 5 millimolar based on the total volume of water and sediment.

3. The method according to claim 1 wherein the halogen-substituted compound is selected from the group consisting of bromine-substituted benzoic acid, bromine-substituted salicylic acid, iodine-substituted benzoic acid, and iodine-substituted salicylic acid.

4. The method of claim 1 wherein the halogen-substituted compound is halogenated benzoic acid or halogenated salicylic acid containing from 1 to 5 chlorine, bromine, or iodine atoms per molecule.

5. The method of claim 4 wherein the halogen substituted compound is 4-bromobenzoic acid or 2,5-dibromobenzoic acid.

* * * * *